US009354180B2

(12) United States Patent
Jiang et al.

(10) Patent No.: US 9,354,180 B2
(45) Date of Patent: May 31, 2016

(54) QUANTIFYING THE LEVEL OF INTERMACROMOLECULAR INTERACTIONS BY USING PYRENE EXCIMER FORMATION

(71) Applicants: Afton Chemical Corporation, Richmond, VA (US); University of Waterloo, Waterloo (CA)

(72) Inventors: Sheng Jiang, Glen Allen, VA (US); Akhilesh Duggal, Magnolia, TX (US); Jean Duhamel, Waterloo (CA); Solmaz Pirouz, Glen Allen, VA (US)

(73) Assignees: Afron Chemical Corporation, Richmond, VA (US); University of Waterloo, Waterloo (CA)

( * ) Notice: Subject to any disclaimer, the term of this patent is extended or adjusted under 35 U.S.C. 154(b) by 0 days.

(21) Appl. No.: 14/854,357

(22) Filed: Sep. 15, 2015

(65) Prior Publication Data
US 2016/0077012 A1    Mar. 17, 2016

Related U.S. Application Data

(60) Provisional application No. 62/051,195, filed on Sep. 16, 2014.

(51) Int. Cl.
| | |
|---|---|
| *G01N 21/64* | (2006.01) |
| *G01N 33/30* | (2006.01) |
| *G01N 21/77* | (2006.01) |
| *G01N 11/00* | (2006.01) |
| *G01N 33/26* | (2006.01) |
| *G01N 33/28* | (2006.01) |

(52) U.S. Cl.
CPC ............... *G01N 21/77* (2013.01); *G01N 11/00* (2013.01); *G01N 21/643* (2013.01); *G01N 33/26* (2013.01); *G01N 21/6428* (2013.01); *G01N 33/2888* (2013.01); *G01N 33/30* (2013.01); *G01N 2011/008* (2013.01); *G01N 2021/7786* (2013.01)

(58) Field of Classification Search
CPC . G01N 21/64; G01N 21/6428; G01N 21/643; G01N 33/26; G01N 33/28; G01N 33/2888; G01N 33/30
USPC ................ 436/164, 172; 73/10, 53.05, 54.01, 73/54.02
See application file for complete search history.

(56) References Cited

U.S. PATENT DOCUMENTS

| | | | | |
|---|---|---|---|---|
| 6,107,257 | A | * | 8/2000 | Valcho .................. C08F 255/00 508/221 |
| 2007/0191242 | A1 | * | 8/2007 | Srinivasan ........... C10M 171/02 508/591 |
| 2012/0101017 | A1 | | 4/2012 | Duggal |

OTHER PUBLICATIONS

[No Author Listed] Excimer. http://en.wikipedia/org/wiki/Excimer. Last modified Jan. 18, 2014. 4 pages.
[No Author Listed] Pyrene. http://en.wikipedia/org/wiki/Pyrene. Last modified Apr. 4, 2014. 3 pages.
Ingratta et al., Correlating Pyrene Excimer Formation with Polymer Chain Dynamics in Solution. Possibilities and Limitations. Macromolecules. 2007;40:6647-6657.
Pirouz et al., Quantifying the Level of Intermacromolecular Interactions in Ethylene-Propylene Copolymers by Using Pyrene Excimer Formation. Macromolecules. 2015;48(13):4620-4630. DOI: 10.1021/acs.macromol.5b00806.
Zhang et al., Characterization by Fluorescence of the Distribution of Maleic Anhydride Grafted onto Ethylene-Propylene Copolymers. Macromolecules. 2004;37:1877-1890.
Zhang et al., Study of maleated ethylene-propylene copolymers by fluorescence: Evidence for succinimide induced polar associations in an apolar solvent. European Polymer Journal. 2008;44:3005-3014.
Zhang et al., Study of the Microcrystallization of Ethylene-Propylene Random Copolymers in Solution by fluorescence. Macromolecules. 2007;40;661-669.

* cited by examiner

*Primary Examiner* — Maureen Wallenhorst
(74) *Attorney, Agent, or Firm* — Wolf, Greenfield & Sacks, P.C.

(57) ABSTRACT

The present invention relates to methods for determining the level of intermolecular interaction of a polymer based on the fraction of intermolecular interaction ($f_{inter}$) relative to the inter, total molecular interaction, which includes both intermolecular and intramolecular interactions. Further provided herein is a method of identifying a suitable viscosity index improver based on the value of $f_{inter}$. The identified suitable viscosity index improver can be used in a lubricating oil composition for, e.g., a power transmission system.

16 Claims, 2 Drawing Sheets

US 9,354,180 B2

QUANTIFYING THE LEVEL OF INTERMACROMOLECULAR INTERACTIONS BY USING PYRENE EXCIMER FORMATION

RELATED APPLICATION

The present application claims priority under 35 U.S.C. §119(e) to U.S. Provisional Patent Application No. 62/051,195, filed Sep. 16, 2014, the content of which is herein incorporated by reference in its entirety.

BACKGROUND OF THE INVENTION

The ability to quantify the level of intermolecular associations between macromolecules in solution is a topic of extreme scientific importance, as such associations typically lead to massive changes in the properties of a polymer solution. For instance, if an associative polymer (AP) associates intramolecularly to form unimolecular polymeric micelles, the AP solution will remain fluid, whereas if the associations take place intermolecularly, the resulting polymeric network will induce a dramatic increase in the solution viscosity. Certainly one of the tools most commonly used to probe intermolecular associations is fluorescence resonance energy transfer or FRET. Since an excited donor (D) can only transfer its energy to a ground-state acceptor (A) if the distance separating D from A ($d_{D-A}$) is less than twice the Förster radius ($R_o$), which is itself less than 10 nm for any given D-A pair, evidence of FRET between a D-labeled macromolecule and an A-labeled macromolecule provides strong evidence of intermacromolecular interactions. The strength of these interactions can be inferred qualitatively from the FRET efficiency ($E_{FRET}$) with $E_{FRET}$ taking values between zero and unity depending on how $d_{D-A}$ averaged over all D-A pairs compares to $R_o$. Interestingly, a quantitative measure of the actual level of association, such as the molar fraction of macromolecules ($f_{inter}$) involved in intermolecular associations, is rarely provided when FRET is used, probably because of the complex relationship that exists between $E_{FRET}$ and the distribution of $d_{D-A}$ values.

SUMMARY OF THE INVENTION

The present disclosure is based on the unexpected development of a rapid and straightforward method to determine the intermolecular interaction of macromolecules (e.g. a polymer) by using fluorescent dye (e.g. pyrene) labeled macromolecules.

Accordingly, one aspect of the present disclosure features a method for determining the level of intermolecular interaction of a polymer, the method comprising: (a) providing a first solution comprising a polymer, which is labelled with a fluorescent dye, (b) providing a second solution comprising the labelled polymer, wherein the concentration of the labelled polymer in the second solution is lower than the concentration of the labelled polymer in the first solution, (c) measuring fluorescence intensities of excimers ($I_E$) and fluorescence intensities of monomers ($I_M$) of the first and second solutions, and (d) determining a level of intermolecular interaction of the polymer based on the ratios between $I_E$ and $I_M$ of the first and second solutions. The method may further comprise, prior to step (c), incubating the first solution and the second solution at room temperature. Step (c) may be performed at various temperatures ranging from about −50° C. to about 100° C.

In some examples, the concentration of the labelled polymer in the first solution is at least 1 g/L and the concentration of the labelled polymer in the second solution is up to 1 g/L. The labelled polymer may contain about 10 to about 1,000 µmol (e.g., 10 to 500 µmol) of the fluorescent dye per gram of the polymer. In some examples, the labelled polymer in the first solution contains 10 to 500 µmol of the fluorescent dye per gram of the polymer. Alternatively or in addition, the labelled polymer in the second solution contains 10 to 500 µmol of the fluorescent dye per gram of the polymer.

In some embodiments, the second solution further comprises an unlabeled polymer, which may be at a concentration of at least 1 g/L. The unlabeled polymer is the same as the polymer moiety of the labeled polymer. Alternatively, the unlabeled polymer is different from the polymer moiety of the labeled polymer.

In the methods described herein, the level of intermolecular interaction of the polymer is determined by a formula set forth as:

$$f_{inter}=[(I_E/I_M)^H-(I_E/I_M)^L]/(I_E/I_M)^H,$$

in which $f_{inter}$ is the fraction of intermolecular interaction relative to the total molecular interaction which includes intermolecular and intra molecular interactions, $(I_E/I_M)^H$ represents the fluorescence intensity ratio of excimer to monomer of the first solution, and $(I_E/I_M)^L$ represents the fluorescence intensity ratio of excimer to monomer of the second solution.

In another aspect, the present disclosure provides a method for determining the level of intermolecular interaction of a polymer, the method comprising: (a) providing a first solution comprising a polymer, which is labelled with a fluorescent dye, (b) providing a second solution comprising the labelled polymer and an unlabeled polymer, wherein the concentration of the labelled polymer in the second solution is lower than or the same as the concentration of the labelled polymer in the first solution and the concentration of the labelled polymer in the second solution is lower than or the same as the concentration of the unlabeled polymer in the second solution, (c) measuring fluorescence intensities of excimers ($I_E$) and fluorescence intensities of monomers ($I_M$) of the first and second solutions, and (d) determining a level of intermolecular interaction of the polymer based on the ratios between $I_E$ and $I_M$ of the first and second solutions.

The level of intermolecular interaction of the polymer is determined by a formula set forth as:

$$f_{inter}=[(I_E/I_M)^H-(I_E/I_M)^L]/(I_E/I_M)^H,$$

in which $f_{inter}$ is the fraction of intermolecular interaction relative to the total molecular interaction which includes intermolecular and intra molecular interactions, $(I_E/I_M)^H$ represents the fluorescence intensity ratio of excimer to monomer of the first solution, and $(I_E/I_M)^L$ represents the fluorescence intensity ratio of excimer to monomer of the second solution.

In some examples, the concentration of the labelled polymer in the first solution is 10 mg/L–10 g/L, the concentration of the labelled polymer in the second solution is 1 mg/L-1 g/L, and the concentration of the unlabeled polymer in the second solution is 2-100 times that of the labelled polymer in the second solution. Alternatively or in addition, the concentration of the unlabeled polymer in the second solution is ten times that of the labelled polymer in the second solution.

Also disclosed herein are methods for identifying a viscosity index improver suitable for use in a lubricant composition.

In some embodiments, the method comprises: (a) providing a first solution comprising a candidate polymer that is labeled by a fluorescent dye, (b) providing a second solution comprising the labeled candidate polymer, wherein the concentration of the labelled polymer in the second solution is lower than the concentration of the labelled polymer in the first solution, (c) measuring fluorescence intensities of excimers ($I_E$) and fluorescence intensities of monomers ($I_M$) of the first and second solutions at a predetermined temperature (e.g., about −30° C. to about 25° C.), (d) determining a level of intermolecular interaction of the candidate polymer based on a formula set forth as:

$$f_{inter}=[(I_E/I_M)^H-(I_E/I_M)^L]/(I_E/I_M)^H,$$

in which $f_{inter}$ is the fraction of intermolecular interaction relative to the total molecular interaction which includes intermolecular and intra molecular interactions, $(I_E/I_M)^H$ represents the fluorescence intensity ratio of excimer to monomer of the first solution, and $(I_E/I_M)^L$ represents the fluorescence intensity ratio of excimer to monomer of the second solution; and (e) selecting the candidate polymer as a viscosity index improver for use in a lubricant composition, if the $f_{inter}$ value of the candidate polymer is lower than a predetermined level. The $f_{inter}$ value is temperature-dependent and the predetermined level may vary at different temperature. A skilled person in the art is readily able to determine this level based on the particular need for a viscosity index improver. For example, at −30° C., the predetermined level is 0.8, or 0.7, or 0.5, or 0.3.

In some examples, the concentration of the labelled polymer in the first solution may be at least 1 g/L and the concentration of the labelled polymer in the second solution is up to 1 g/L. Alternatively or in addition, the second solution further comprises an unlabeled polymer at a concentration of at least 1 g/L. The unlabeled polymer may be the same as the labeled polymer. Alternatively, the unlabeled polymer is different from the labeled polymer.

In some examples, the labelled polymer contains 10-1,000 μmol of the fluorescent dye per gram of the polymer. For example, the first solution contains 10 to 500 μmol of the fluorescent dye per gram of the polymer. Alternatively or in addition, the second solution contains 10 to 500 μmol of the fluorescent dye per gram of the labelled polymer.

In other embodiments, a method for identifying a viscosity index improver suitable for use in a lubricant composition may comprise: (a) providing a first solution comprising a candidate polymer that is labeled by a fluorescent dye, (b) providing a second solution comprising the labelled polymer and an unlabeled polymer, wherein the concentration of the labelled polymer in the second solution is lower than or the same as the concentration of the labelled polymer in the first solution and the concentration of the labelled polymer in the second solution is lower than or the same as the concentration of the unlabeled polymer in the second solution, (c) measuring fluorescence intensities of excimers ($I_E$) and fluorescence intensities of monomers ($I_M$) of the first and second solutions at a predetermined temperature, (d) determining a level of intermolecular interaction of the candidate polymer based on the formula set forth as:

$$f_{inter}=[(I_E/I_M)^H-(I_E/I_M)^L]/(I_E/I_M)^H,$$

in which $f_{inter}$ is the fraction of intermolecular interaction relative to the total molecular interaction which includes intermolecular and intra molecular interactions, $(I_E/I_M)^H$ represents the fluorescence intensity ratio of excimer to monomer of the first solution, and $(I_E/I_M)^L$ represents the fluorescence intensity ratio of excimer to monomer of the second solution; and (e) selecting the candidate polymer as a viscosity index improver for use in a lubricant composition, if the $f_{inter}$ value of the candidate polymer is lower than a predetermined level. For example, at −30° C., the predetermined level is 0.8, or 0.7, or 0.5, or 0.3.

The concentration of the labelled polymer in the first solution is 10 mg/L-10 g/L, the concentration of the labelled polymer in the second solution is 1 mg/L-1 g/L, and the concentration of the unlabeled polymer in the second solution is 2-100 times that of the labelled polymer in the second solution. In some examples, the concentration of the unlabeled polymer in the second solution is ten times that of the labelled polymer in the second solution.

In any of the methods described herein, the fluorescent dye may be pyrene. $I_M$ and $I_E$ may be measured by a spectrofluorometer In any of the methods described herein, the polymer can be a polyolefin or an olefin copolymer. Exemplary polyolefin polymers include, but are not limited to, polyethylene (PE), polypropylene (PP), hydrogenated polyisoprene, hydrogenated polybutadiene, polyisobutene, hydrogenated styrene butadiene copolymer, and hydrogenated styrene isoprene copolymer. In one example, the polymer is an olefin copolymer, which is a PE/PP copolymer.

In any of the methods described herein, the labelled polymer can be prepared by reacting a grafted polyolefin or olefin copolymer with the fluorescent dye. For example, the grafted polyolefin or olefin copolymer can be maleated, e.g., maleated with maleic anhydride.

In any of the methods described herein, the first solution and the second solution can be irradiated at a wavelength of 200-350 nm to generate corresponding emission spectra, which may be acquired at a wavelength of 350-600 nm. In some examples, $I_M$ and $I_E$ are measured by a spectrofluorometer. In one example, $I_M$ is measured at a wavelength of 372-378 nm and k is measured at a wavelength of 500-530 nm.

The details of one or more embodiments of the invention are set forth in the description below. Other features or advantages of the present invention will be apparent from the following drawings and detailed description of several embodiments, and also from the appended claims.

and EP(SM) (10 g/L) as a function of temperature. Plot of $I_E/I_M$ as a function of temperature for (C) Py-EP(SM) (10 g/L) and d) a mixture of Py-EP(SM) (0.1 g/L) and EP(SM) (10 g/L).

Figure 2:
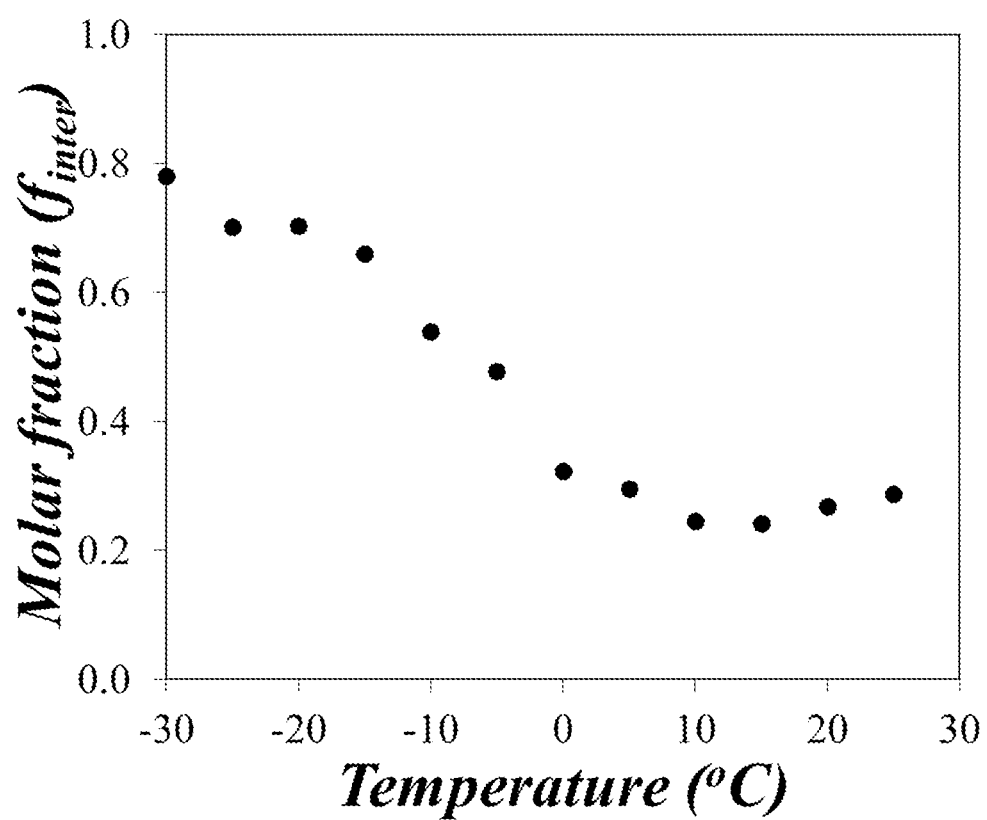

FIG. 2. Plot of the fraction of intermolecular interaction $f_{inter}$ of pyrene labels forming excimer intermolecularly for Py-EP(SM) as a function of temperature.

DETAILED DESCRIPTION OF THE INVENTION

The present disclosure provides a method for determining the level of intermolecular interaction of a polymer and relying on such a value to identify viscosity index improvers that are suitable for use in, e.g., lubricating oils, which may be used in automobile industry, e.g., as multigrade engine oils, gear oils, automatic transmission fluids, power steering fluids, or hydraulic fluids. Suitable viscosity index improvers identified in any of the methods described herein may be added to lubricant compositions to reduce the change of viscosity at high or low temperatures.

I. Methods for Determining Level of Intermolecular Interaction of Polymers

The method described herein may involve two solutions comprising a polymer labelled with a fluorescent dye at different concentrations, one of which is lower than the other. The first solution (the high concentration solution) contains the labeled polymer at a higher concentration (e.g., at least about 1 g/L, for example, at least about 5 g/L) and the second solution (the low concentration solution) comprises the labeled polymer at a concentration (e.g., up to about 1 g/L) that may be lower than that in the high concentration solution.

The high concentration solution, the low concentration solution, or both may comprise a suitable solvent. In some embodiments, the solvents for the high concentration and low concentration solution are the same. In other embodiments, the high concentration solution and the low concentration solution may contain different solvents. Suitable solvents for the high concentration solution, the low concentration solution, or both can be an aprotic solvent, e.g., aprotic polar solvents or aprotic non-polar solvents. In certain embodiments, suitable solvents can both solubilize the polymer in the high concentration solution and the low concentration solution respectively. In certain embodiments, suitable solvents can solubilize the EP (ethylene propylene) copolymer. In certain embodiments, suitable solvents can solubilize the EP copolymer having the succinimide group. In certain embodiments, the suitable solvents include, but are not limited to, toluene, xylene, benzene, or tetrahydrofuran (THF).

The high concentration solution may comprise the labeled polymer as the only polymer components in the high concentration solution. In some embodiments, the high concentration solution can contain the labeled polymer at a concentration of at least about 6 g/L, e.g., 7 g/L, 8 g/L, 9 g/L, 10 g/L, 15 g/L, or 20 g/L. In some embodiments, the concentration of the labeled polymer in the high concentration solution can range from about 1 g/L to about 100 g/L, e.g., about 3 g/L to about 100 g/L; e.g., about 5 g/L to about 100 g/L; about 5 g/L to about 50 g/L; about 8 g/L to about 50 g/L; about 5 g/L to about 20 g/L. In one example, the concentration of the labeled polymer in the high concentration solution is about 5 g/L, about 10 g/L, or about 15 g/L.

Alternatively or in addition, the second solution may contain the labeled polymer at a concentration of up to 0.8 g/L, e.g., 0.6 g/L, 0.5 g/L, 0.3 g/L, 0.2 g/L; 0.1 g/L, 0.08 g/L, 0.05 g/L, or 0.01 g/L. In some embodiments, the concentration of the labeled polymer in the low concentration solution can range from about 0.01 g/L to about 10 g/L; e.g., 0.03 g/L to about 5 g/L; about 0.05 to about 1 g/L; about 0.05 g/L to about 0.5 g/L; or about 0.08 g/L to about 0.2 g/L. In one example, the concentration of the labeled polymer in the low concentration solution is about 0.01 g/L, about 0.05 g/L, about 0.1 g/L; or about 0.3 g/L.

In some embodiments, the high concentration solution contains a fluorescent dye labeled polymer at a concentration of at least about 8 g/L and the low concentration solution contains a fluorescent dye labeled polymer at a concentration up to about 0.5 g/L. In some embodiments, the high concentration solution contains a fluorescent dye labeled polymer at a concentration of at least about 10 g/L and the low concentration solution contains a fluorescent dye labeled polymer at a concentration up to about 0.11 g/L.

In some embodiments, the low concentration solution may comprise an unlabeled polymer, which can be either the same as the polymer moiety in the labeled polymer or different from the polymer moiety in the labelled polymer. The concentration of the labeled polymer in the low concentration solution may be lower than or the same as the concentration of the labeled polymer in the high concentration solution and is lower than or the same as the concentration of the unlabeled polymer in the low concentration solution. In some examples, the concentration of the unlabeled polymer in the low concentration solution ranges from about 1 g/L to about 500 g/L; e.g., about 3 g/L to about 200 g/L, about 5 g/L to about 100 g/L, about 8 g/L to about 50 g/L; or about 10 g/L to about 20 g/L. In one example, the concentration of the unlabeled polymer in the low concentration solution is about 5 g/L, about 10 g/L, about 15 g/L, or about 20 g/L.

In one example, the labeled polymer in the high concentration solution can range from about 10 mg/L to 10 g/L, the labeled polymer in the low concentration solution can range from about 1 mg/L to 1 g/L, and the concentration of the unlabeled polymer in the low concentration solution can be about 2-100 times (e.g., about 5 times, 10 times, or 20 times) that of the labeled polymer in the low concentration solution.

In some embodiments, the labeled polymer in the high concentration solution, the low concentration solution, or both may contain about 5 to 1,000 µmol of the fluorescent dye per gram of the polymer; e.g., about 10 to 1,000 µmol of the fluorescent dye per gram of the polymer; 10 to 800 µmol of the fluorescent dye per gram of the polymer, e.g., 10 to 500 µmol of the fluorescent dye per gram of the polymer, 10 to 300 µmol of the fluorescent dye per gram of the polymer; 10 to 200 µmol of the fluorescent dye per gram of the polymer; 10 to 100 µmol of the fluorescent dye per gram of the polymer prior to labeling; 50 to 700 µmol of the fluorescent dye per gram of the polymer; 100 to 600 µmol of the fluorescent dye per gram of the polymer; 150 to 500 µmol of the fluorescent dye per gram of the polymer; or 200 to 400 µmol of the fluorescent dye per gram of the polymer.

In some examples, the labeled polymer in the high concentration solution may contain 10 to 500 µmol (e.g., about 10-200, 10-300, or 100-400 µmol) of the fluorescent dye per gram of the polymer. Alternatively or in addition, the labeled polymer in the low concentration solution may contain 10 to 500 μmol (e.g., about 10-200, 10-300, or 100-400 μmol) of the fluorescent dye per gram of the polymer.

As used herein, a fluorescent dye (also known herein as fluorochromes and fluorophores) is a compound or molecule that luminesces. Typically fluorescent dyes absorb electromagnetic energy at one wavelength and emit electromagnetic energy at a second wavelength. Examples of fluorescent compounds include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, and Texas Red-X. (See, e.g., Handbook of Fluorescent Probes and Research Products, 8th Edition, Molecular Probes Inc.) In certain embodiments, the fluorescent dye is Pyrene. In certain embodiments, the fluorescent dye is naphthalene.

As used herein, the polymer can be polyolefin or olefin copolymer, which can be modified with a reactive group (e.g., grafted polymer or copolymer) for conjugating with a fluorescent dye. For example, the polymer can be polyethylene (PE), polypropylene (PP), hydrogenated polyisoprene, hydrogenated polybutadiene, polyisobutene, hydrogenated styrene butadiene copolymer, or hydrogenated styrene isoprene copolymer. In some examples, the polymer can be an olefin copolymer, which may be a PE/PP copolymer.

Exemplary reactive groups include, but are not limited to, carboxylic acid, hydroxyl, alkenyl, alkynyl, amino, or epoxyl.

In some embodiments, the grafted polyolefin or olefin copolymer reacts with a carboxylic reactant to form an acylated copolymer (see U.S. Pat. No. 6,107,257, incorporated herein by reference), which may be an acylated ethylene copolymer. In some embodiments, the carboxylic reactant has at least one ethylenic bond and at least one carboxylic acid or its anhydride groups or a polar group which is convertible into the carboxyl groups by oxidation or hydrolysis. Exemplary carboxylic reactants include, but are not limited to, acrylic, methacrylic, cinnamic, crotonic, maleic, fumaric and itaconic reactants. In some examples, the carboxylic reactants can be maleic acid, fumaric acid, maleic anhydride, and a mixture of two or more of these.

In some embodiments, the unsaturated ethylene copolymers or terpolymers may react with a suitable carboxylic reactant such as caritaconic acid or its anhydride due to its reduced tendency to form a cross-linked structure during the free-radical grafting process. The ethylenically unsaturated carboxylic acid may provide one or two carboxylic groups per mole of reactant to the grafted polymer. For example, methyl methacrylate can provide one carboxylic group per molecule to the grafted polymer while maleic anhydride can provide two carboxylic groups per molecule to the grafted polymer.

The grafting reaction to form the acylated olefin copolymers is generally carried out with the aid of a free-radical initiator either in solution or in bulk, as in an extruder or intensive mixing device. When the polymerization is carried out in hexane solution, it is economically convenient to carry out the grafting reaction in hexane as described in U.S. Pat. Nos. 4,340,689, 4,670,515 and 4,948,842, incorporated herein by reference. The resulting polymer intermediate is characterized by having carboxylic acid acylating functionality randomly within its structure.

In a bulk process for forming the acylated olefin copolymers, the olefin copolymer may be fed to rubber or plastic processing equipment such as an extruder, intensive mixer or masticator, heated to a temperature of 150 to 400° C. and the ethylenically unsaturated carboxylic acid reagent and free-radical initiator are separately co-fed to the molten polymer to effect grafting. The reaction may be carried out optionally with mixing conditions to effect shearing and grafting of the ethylene copolymers according to U.S. Pat. No. 5,075,383, incorporated herein by reference. The processing equipment is generally purged with nitrogen to prevent oxidation of the polymer and to aid in venting unreacted reagents and byproducts of the grafting reaction. The residence time in the processing equipment may be sufficient to provide for the desired degree of acylation and to allow for purification of the acylated copolymer via venting. Mineral or synthetic lubricating oil may optionally be added to the processing equipment after the venting stage to dissolve the acylated copolymer.

The free-radical initiators which may be used to graft the ethylenically unsaturated carboxylic acid material to the polymer backbone include peroxides, hydroperoxides, peresters, and also azo compounds and preferably those which have a boiling point greater than 100° C. and decompose thermally within the grafting temperature range to provide free radicals. Representatives of these free-radical initiators are azobutyronitrile, dicumyl peroxide, 2,5-dimethylhexane-2,5-bis-tertiarybutyl peroxide and 2,5-dimnethylhex-3-yne-2,5-bis-tertiary-butyl peroxide. The initiator is used in an amount of between about 0.005% and about 1% by weight based on the weight of the reaction mixture.

Other methods known in the art for effecting reaction of ethylene-olefin copolymers with ethylenically unsaturated carboxylic reagents, such as halogenation reactions, thermal or "ene" reactions or mixtures thereof, can be used instead of the free-radical grafting process. Such reactions are conveniently carried out in mineral oil or bulk by heating the reactants at temperatures of 250 to 400° C. under an inert atmosphere to avoid the generation of free radicals and oxidation byproducts. "Ene" reactions are a preferred method of grafting when the ethylene-olefin copolymer contains unsaturation. To achieve the high graft levels, 0.3 to 0.5 carboxylic groups per 1000 Mn, desired by this invention it may be necessary to follow or proceed the "ene" or thermal graft reaction with a free radical graft reaction.

In some embodiments, the carboxylic reactant is grafted onto the polymer backbone in an amount to provide 0.3 to 0.75 carboxylic groups per 1000 number average molecular weight units of the polymer backbone. In some embodiments, the carboxylic reactant is grafted onto the polymer backbone in an amount to provide 0.3 to 0.5 carboxylic groups per 1000 number average molecular weight. For example, a copolymer substrate with Mn of 20,000 is grafted with 6 to 15 carboxylic groups per polymer chain or 3 to 7.5 moles of maleic anhydride per mole of polymer. A copolymer with Mn of 100,000 is grafted with 30 to 75 carboxylic groups per polymer chain or 15 to 37.5 moles of maleic anhydride per polymer chain.

In some embodiments, a labelled polymer as described herein can be prepared from reacting a grafted polyolefin or olefin copolymer with a suitable fluorescent dye. In some embodiments, the grafted polyolefin or olefin copolymer is maleated before reacting the fluorescent dye. In some embodiments, the grafted polyolefin or olefin copolymer is maleated with maleic anhydride. In some embodiments, the grafted polyolefin or olefin copolymer is maleated before reacting the fluorescent dye.

As used herein, polyolefin (PO) refers to a class of polymers produced from an olefin (also called an alkene with the general formula $C_nH_{2n}$, n is an integer from 2 inclusive) as a monomer. Polyolefin (PO) includes but is not limited to, straight chain and branched, polyethylene (PE), polypropylene (PP), hydrogenated polyisoprene, polybutadiene, hydrogenated polybutadiene, and polyisobutene, hydrogenated styrene butadiene copolymer, and hydrogenated styrene isoprene copolymer. In certain embodiments, the polyolefin is polypropylene (PP). In certain embodiments, the polyolefin is polyethylene (PE).

A copolymer refers to a polymer derived from more than one species of monomer. As used herein, olefin copolymer (OC) refers to a copolymer derived from at least two monomers with at least one monomer having at least one alkenyl group. In some embodiments, the olefin copolymer is derived from ethylene and at least one other alpha-olefin having from 3 to about 28 carbon atoms, i.e., one of the formula $CH_2CHR_a$ wherein $R_a$ is C1-C30 straight chain or branched chain alkyl. In some embodiments, the olefin copolymer is derived from ethylene and at least one other alpha-olefin of the formula $CH_2CHR_a$ wherein $R_a$ is C1-C8 straight chain or branched chain alkyl. In some embodiments, the olefin copolymer is derived from ethylene and at least one other alpha-olefin of the formula $CH_2CHR_a$ wherein $R_a$ is C1-C3 straight chain or branched chain alkyl. In some embodiments, the olefin copolymer is an ethylene-propylene copolymer. In some embodiments, the olefin copolymer is an ethylene-1-butene copolymer.

Graft copolymers refer to branched copolymers in which the side chains are structurally distinct from the main chain. The individual chains of a graft copolymer may be homopolymers or copolymers.

Grafted polyolefin or co-polyolefin refers to chemically bonded two or more types of polyolefin or co-polyolefin. In some embodiments, the grafting is anhydride grafting. In some embodiments, the grafting is succinimide anhydride grafting.

In some embodiments, the copolymer is ethylene copolymer or terpolymer. These materials may contain minor amounts of other olefinic monomers so long as the basic characteristics of the ethylene copolymers are not materially changed.

In some embodiments, the polymers for use in the present invention are copolymers of ethylene and one or more C3 to C23 alpha-olefins (U.S. Pat. No. 6,107,257, incorporated by reference). In some embodiments, the polymers for use in the present invention are copolymers of ethylene and propylene. Other alpha-olefins suitable in place of propylene to form the copolymer or to be used in combination with ethylene and propylene to form a terpolymer include 1-butene, 1-pentene, 1-hexene, 1-octene and styrene; α,ω-diolefins such as 1,5-hexadiene, 1,6-heptadiene, 1,7-octadiene; branched chain alpha-olefins such as 4-methylbutene-1,5-methylpentene-1 and 6-methylheptene-1; and mixtures thereof.

In some embodiments, the polymers for use in the methods described herein are interpolymers, which may be prepared using a third component. The third component generally used to prepare an interpolymer substrate is a polyene monomer selected from non-conjugated dienes and trienes. The non-conjugated diene component is one having from 5 to 14 carbon atoms in the chain. In some embodiments, the diene monomer is characterized by the presence of a vinyl group in its structure and can include cyclic and bicyclo compounds. Representative dienes include 1,4-hexadiene, 1,4-cyclohexadiene, dicyclopentadiene, 5-ethylidene-2-norbornene, 5-methylene-2-norborene, 1,5-heptadiene, and 1,6-octadiene. In some embodiments, a mixture of more than one diene can be used in the preparation of the interpolymer. In some embodiments, the non-conjugated diene for preparing a terpolymer or interpolymer substrate is 1,4-hexadiene. In some embodiments, the triene component has at least two non-conjugated double bonds, and up to about 30 carbon atoms in the chain. The trienes useful in preparing the interpolymer of the invention include, but are not limited to 1-isopropylidene-3α,4,7,7α-tetrahydroindene, 1-isopropylidenedicyclopentadiene, dihydro-isodicyclopentadiene, and 2-(2-methylene-4-methyl-3-pentenyl)[2.2.1]bicyclo-5-heptene.

As used herein, ethylene-propylene or higher alpha-olefin copolymers may consist of from about 15 to 80 mole percent ethylene and from about 85 to 20 mole percent C3 to C23 alpha-olefin. In some embodiments, ethylene-propylene or higher alpha-olefin copolymers may have about 35 to 75 mole percent ethylene and about 65 to 25 mole percent of a C3 to C23 alpha-olefin. In some embodiments, ethylene-propylene or higher alpha-olefin copolymers may have about 50 to 70 mole percent ethylene and about 50 to 30 mole percent C3 to C23 alpha-olefin. In some embodiments, ethylene-propylene or higher alpha-olefin copolymers may have about 55 to 65 mole percent ethylene and 45 to 35 mole percent C3 to C23 alpha-olefin. In some embodiments, the terpolymer variations of the polymers described herein may contain from about 0.1 to 10 mole percent of a non-conjugated diene or triene. In certain embodiments, the ethylene copolymer or terpolymer, is an oil-soluble, linear or branched polymer having a number average molecular weight from about 20,000 to 150,000 as determined by gel permeation chromatography and universal calibration standardization. In certain embodiments, the ethylene copolymer or terpolymer has an average molecular weight of 30,000 to 110,000.

In some embodiments, the ethylene-olefin copolymer is formed by polymerization in the Ziegler-Natta or metallocene catalyst system. The polymerization medium can include solution, slurry, or gas phase processes. When solution polymerization is employed, the solvent may be any suitable inert hydrocarbon solvent that is liquid under reaction conditions for polymerization of alpha-olefins; examples of satisfactory hydrocarbon solvents include straight chain paraffins having from 5 to 8 carbon atoms. In some embodiments, the solvent used in polymerization is hexane. In some embodiments, the solvent used in polymerization is an aromatic hydrocarbon solvent. In some embodiments, the solvent used in polymerization is an aromatic hydrocarbon having a single benzene nucleus (e.g. benzene, toluene and etc). In some embodiments, the solvent used in polymerization is a saturated cyclic hydrocarbon solvent having boiling point ranges approximating those of the straight chain paraffinic hydrocarbons and aromatic hydrocarbons as described herein. The solvent selected may be a mixture of one or more of the foregoing hydrocarbons. When slurry polymerization is employed, the liquid phase for polymerization is liquid propylene. In some embodiments, the polymerization medium is free of substances that will interfere with the catalyst components.

In some embodiments, any of the polymers described herein, including polyolefin (PO), olefin copolymer (OC), grafted polyolefin or co-polyolefin, has a number average molecular weight (Mn) (e.g., determined by gel-permeation chromatography employing polystyrene standards) ranging from about 7,000 to about 500,000, e.g., 10,000 to about 400,000, 50,000 to about 300,000, or 100,000 to about 200,000.

In certain embodiments, the pyrene-labeled polymer is pyrene-labeled polyolefin. In certain embodiments, the pyrene-labeled polymer is pyrene-labeled copolymer. In certain embodiments, the pyrene-labeled polymer is pyrene-labeled olefin copolymer. In certain embodiments, the pyrene-labeled polymer is pyrene-labeled grafted polylefin or copolyolefin. In certain embodiments, the pyrene-labeled polymer is pyrene-labeled grafted polylefin or copolyolefin comprising a reactive group modification.

In certain embodiments, the pyrene-labeled polymer is pyrene-labeled polypropylene (PP) or polyethylene (PE). In certain embodiments, the pyrene-labeled polymer is pyrene-labeled polypropylene. In certain embodiments, the pyrene-labeled polymer is pyrene-labeled polyethylene. In certain embodiments, the pyrene-labeled polymer is pyrene-labeled ethylene-propylene copolymer. In certain embodiments, the pyrene-labeled polymer is pyrene-labeled copolyolefin comprising a reactive group modification. In certain embodiments, the pyrene-labeled polymer is pyrene-labeled copolyolefin comprising a reactive group modified by maleation. Maleation, as used herein, refers to the reaction of the polymer with succinic anhydride under suitable condition to generate polymers having succinic anhydride moiety along the polymer backbone (Zhang et al., Macromolecules, 2004, 37, p 1877-1890).

The labelled polymer can be prepared from reacting a grafted polyolefin or olefin copolymer with a fluorescent dye. In some embodiments, the grafted polyolefin or olefin copolymer is directed attached to a fluorescent dye. In some embodiments, the grafted polyolefin or olefin copolymer is attached to a fluorescent dye through a linker.

In certain embodiments, the linker is a cyclic or acyclic, branched or unbranched, substituted or unsubstituted alkylene. In certain embodiments, the linker is a cyclic or acyclic, branched or unbranched, substituted or unsubstituted alkenylene. In certain embodiments, the linker is a cyclic or acyclic, branched or unbranched, substituted or unsubstituted alkynylene. In certain embodiments, the linker is a cyclic or acyclic, branched or unbranched, substituted or unsubstituted heteroalkylene. In certain embodiments, the linker is a cyclic or acyclic, branched or unbranched, substituted or unsubstituted heteroalkenylene. In certain embodiments, the linker is a cyclic or acyclic, branched or unbranched, substituted or unsubstituted heteroalkynylene. In certain embodiments, the linker is a substituted or unsubstituted arylene. In certain embodiments, the linker is a substituted or unsubstituted heteroarylene. In certain embodiments, the linker is a substituted or unsubstituted acylene.

For example, in certain embodiments, the linker is cyclic or acyclic, branched or unbranched, substituted or unsubstituted heteroalkylene of one of the following formulae:

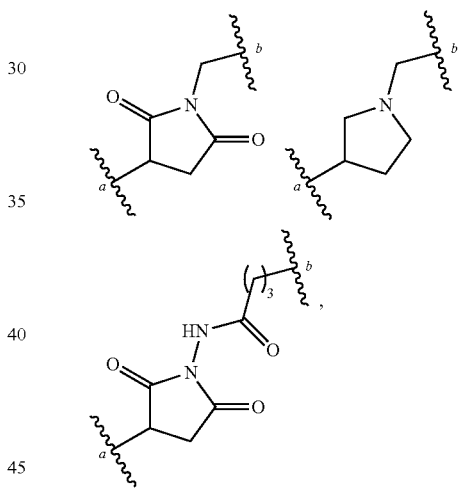

wherein a indicates point of attachment to the polymer and b indicates the point of attachment to the fluorescent dye.

The grafted polyolefin or olefin copolymer may comprise a reactive group modification (e.g., maleation). In certain embodiments, the grafted polyolefin or olefin copolymer is maleated before reacting the fluorescent dye. In certain embodiments, the grafted polyolefin or olefin copolymer is maleated with maleic anhydride before reacting with the fluorescent dye. In certain embodiments, the maleated polymer reacts with the amino group of a fluorescent dye. In certain embodiments, the maleated polymer (e.g. EP-MAH) reacts with 1-pyrenemethyl amine, 1-naphthalenemetylamine, 1-pyrenebutanoic acid hydrazide, or any combinations thereof. In some embodiments, the labeled polymer prepared from EP-MAH is pyrene-labelled (Py-EP), naphthalene-labelled (Np-EP), or doubly-labelled (Py-Np-EP) EP copolymer. In certain embodiments, the carbonyl group of the succinimide linkers of Py-EP is reduced to yield a pyrrolidine linker (see Zhang et al., Eur. Polymer J. 2008, 44, p 3005-3014; Zhang et al., Macromolecules, 2004, 37, p 1877-1890).

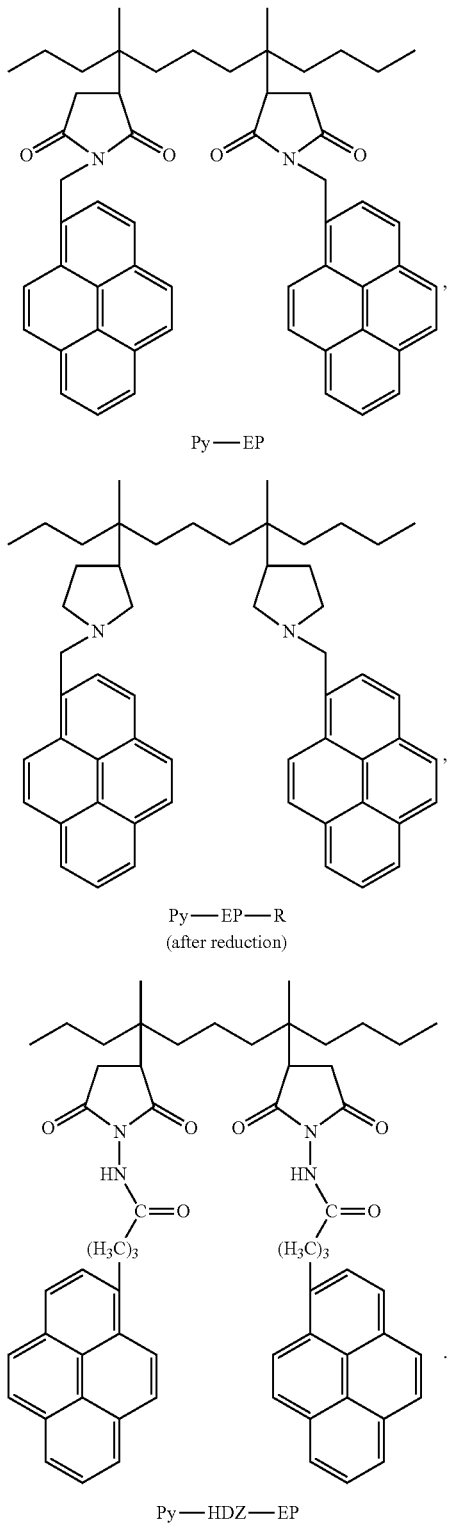

To determine the intermolecular interaction of a polymer, the fluorescence intensities of excimers ($I_E$) and those of monomers ($I_M$) of the high concentration solution and low concentration solution, both comprising the polymer labeled with a fluorescent dye, can be measured and the ratio between $I_E$ and $I_M$ indicates the intermolecular interaction level of the polymer.

In certain embodiments, a steady-state spectrofluorometer is used to measure the luminescence of the polymer labeled with a fluorescent dye. In certain embodiments, a Photon Technology International (PTI) LS-100 steady-state fluorometer equipped with an Ushio UXL-75Xe Xenon arc lamp and a PTI 814 photomultiplier detection system is used to acquire the fluorescence spectra.

In some embodiments, the fluorescence measurements are carried out at temperatures ranging from about −50° C. to about 100° C. (e.g., about −30° C. to about 80° C.; about −30° C. to about 50° C.; or about −25° C. to about 25° C.).

The fluorescence intensities of $I_E$ and $I_M$ may be determined from the fluorescence spectrum of the labeled polymer by integrating the fluorescence spectrum over a wavelength range where the dye monomer and the dye excimer are known to emit as separate entities (i.e. no spectral overlap between the monomer and excimer fluorescence). For example, the part of the fluorescence spectrum where the pyrene monomer is known to emit with as little as possible interference from the excimer fluorescence is the first peak of the fluorescence spectrum between 372 and 378 nm. Similarly, the excimer is known to emit with no interference from the monomer signal over the wavelength range 500-530 nm of the fluorescence spectrum.

In some embodiments, the fluorescence of the high concentration solution, the low concentration solution, or both can be irradiated at a wavelength of 200-350 nm, e.g., 230-320 nm or 250-300 nm, to generate emission spectra.

Alternatively or in addition, the fluorescence of the high concentration solution, the low concentration solution, or both can be acquired at a wavelength ranging from about 350-600 nm, e.g., about 350-500 nm, about 350-400 nm, about 500-600 nm, about 500-530 nm. In some examples, the excimer fluorescence ($I_E$) is measured at a wavelength of 500-530 nm, and/or the monomer fluorescence ($I_M$) is measured at a wavelength of 372-378 nm.

In some instances, the level of intermolecular interaction of the polymer can be determined by the following formula:

$$f_{inter} = [(I_E/I_M)^H - (I_E/I_M)^L]/(I_E/I_M)^H,$$

in which $f_{inter}$ represents the fraction of intermolecular interaction relative to the total molecular interaction, which includes both the intermolecular interaction and the intramolecular interaction; $(I_E/I_M)^H$ represents the fluorescence intensity ratio of excimer to monomer of the high concentration solution, and $(I_E/I_M)^L$ represents the fluorescence intensity ratio of excimer to monomer of the low concentration solution.

II. Identification of Suitable Viscosity Index Improvers

Any of the methods described herein may be applied to identify suitable viscosity index improvers, such as those that are suitable for use as additives in lubricating oils to reduce viscosity changes at high or low temperatures. Such suitable viscosity index improvers may be used as additives in e.g., engine oil, for minimizing the thinning of the engine oils that occurs at high temperature during operation of an automotive.

Whether a candidate polymer can be a suitable viscosity index improvers as described herein may be identified based on the level of its intermolecular interaction as determined by the methods described herein. In some embodiments, the level of intermolecular interaction can be represented by the fraction of intermolecular interaction ($f_{inter}$), which can be calculated by the following formula:

$$f_{inter} = [(I_E/I_M)^H - (I_E/I_M)^L]/(I_E/I_M)^H,$$

in which $f_{inter}$ represents the fraction of intermolecular interaction relative to the total molecular interaction, which includes both the intermolecular interaction and the intramolecular interaction; $(I_E/I_M)^H$ represents the fluorescence intensity ratio of excimer to monomer of the high concentration solution, and $(I_E/I_M)^L$ represents the fluorescence intensity ratio of excimer to monomer of the low concentration solution. When the $f_{inter}$ value of a candidate polymer is lower than a predetermined value based on the $I_E$ and $I_M$ values measured at a predetermined temperature, that candidate polymer is identified as a suitable viscosity index improver, e.g., for the purposes as described herein.

Fraction of intermolecular interaction ($f_{inter}$) can be a measurement to quantify the intermolecular association of polymer chains in solution, which is affected by polymer characteristics, polymer concentration and temperature. When $f_{inter}$ of a polymer is high at a certain temperature, lubricant oil made with the polymer tends to form aggregates between polymer chains and result in gelation under certain conditions. Gelation can be an issue for lubricant oil applications (see U.S. Pat. No. 8,415,284, incorporated by reference).

In some embodiments, the predetermined value of $f_{inter}$ is 0.8 (e.g., 0.7, 0.6, 0.5, 0.4, 0.3, 0.2, or 0.1). If the $f_{inter}$ of a candidate polymer as determined at a predetermined is lower than the predetermined value (e.g., lower than 0.8, lower than 0.7, lower than 0.5, or lower than 0.3), the candidate polymer is identified as a suitable viscosity index improver. The predetermined temperature can range from about −30° C. to about 30° C. (e.g., about −30° C. to about 25° C.; about −5° C. to about 25° C.; or about 0° C. to about 25° C.). In some examples, the predetermined temperature is −30° C., −15° C., 0° C., 10° C., 15° C., or 25° C. and the cutoff $f_{inter}$ value is 0.8. In other examples, the predetermined temperature is −30° C., −15° C., 0° C., 10° C., 15° C., or 25° C. and the cutoff $f_{inter}$ value is 0.7. In yet other examples, the predetermined temperature is −30° C., −15° C., 0° C., 10° C., 15° C., or 25° C. and the cutoff $f_{inter}$ value is 0.5.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Conditions to Collect the Fluorescence Spectra

To avoid the inner filter effect when acquiring the fluorescence spectra, a triangular cell was used for front-face geometry measurements at Py-EP concentrations whose absorbance was higher than 0.1 at 344 nm where pyrene absorbs. Below this concentration, a square cell was used to acquire the fluorescence spectra with the right-angle geometry. All solutions were degassed for 30-40 min under a gentle flow of $N_2$ to remove oxygen. The solutions were excited at a wavelength of 344 nm, and the emission spectrum was acquired from 350 to 600 nm. The fluorescence intensity of the monomer ($I_M$) and excimer ($I_E$) were obtained by integrating the fluorescence spectrum between 372 to 378 nm and 500 to 530 nm, respectively. The fluorescence measurements were also carried out at temperatures ranging from −30±0.2° C. to 25±0.2° C. using a cryostat from Oxford Instruments (Optistat DN) which was coupled to the steady-state fluorometer. Before each measurement, the Py-EP solution was heated to room temperature to erase all pre-association history. The solution was then cooled inside the cryostat. After the set temperature of the cryostat had been reached, the solution was left to equilibrate in the cryostat for 10 min before any fluorescence spectrum was acquired.

Procedure for Running the Spectrofluorometer and Cryostat

A Photon Technology International (PTI) LS-100 steady-state fluorometer equipped with an Ushio UXL-75Xe Xenon arc lamp and a PTI 814 photomultiplier detection system was used to acquire the fluorescence spectra. The procedure provided in the manual of the instruments was followed.

Sample Measurement

Figure 1:
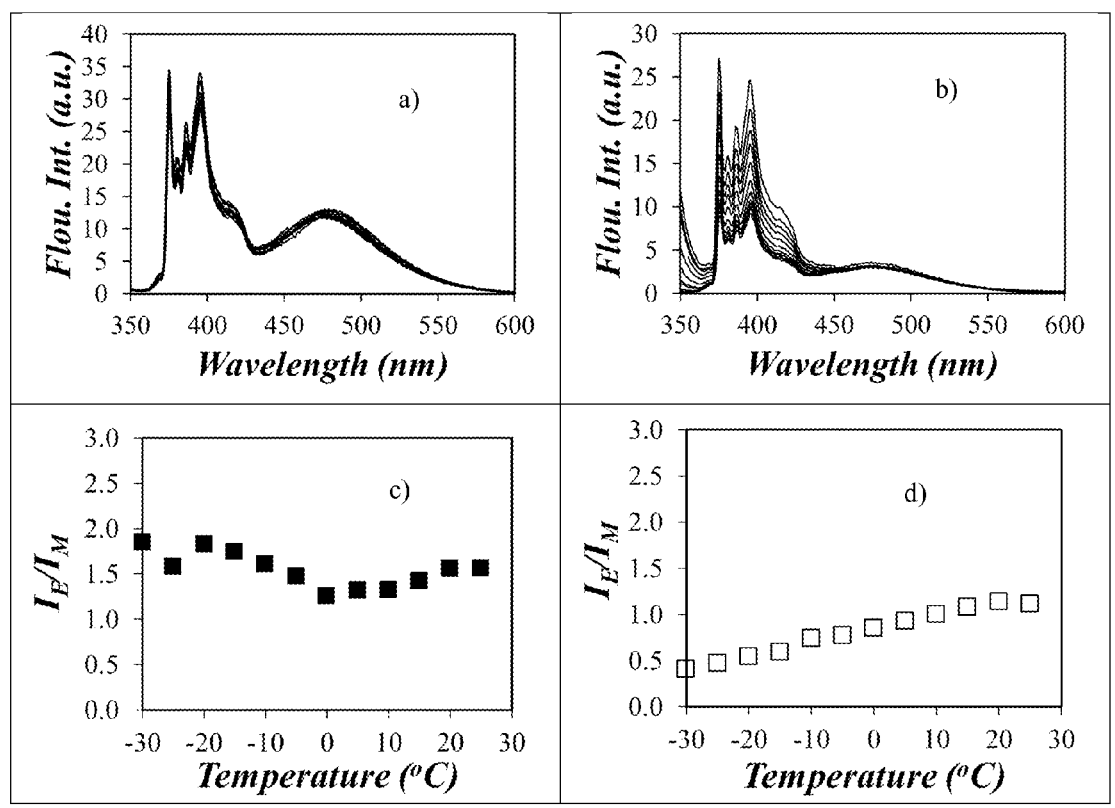
FIG. 1. Fluorescence spectra of toluene solutions of a) Py-EP(SM) (10 g/L) and b) a mixture of Py-EP(SM) (0.1 g/L)

The steady-state fluorescence spectra of a sample of pyrene-labeled semicrystalline ethylene propylene copolymer (Py-EP(SM)) in toluene at a concentration of 10 g/L and 0.01 g/L at temperatures ranging from about −30° C. to about 25° C. are shown in FIGS. 1a and b, respectively.

Sample Calculation

The purpose of these fluorescence experiments is to estimate the fraction of pyrene labels that form excimer intermolecularly. The procedure consists of two sets of experiments. For the first set of experiments, a 10 g/L Py-EP(SM) solution was prepared in toluene. At high (H) concentration of pyrene-labeled macromolecule, the $I_E/I_M$ ratio is referred to as $(I_E/I_M)^H$ and it reflects the local pyrene concentration $[Py]_{loc}$ resulting from intra and intermolecular associations. In a second set of experiments, a 0.01 g/L Py-EP(SM) solution was mixed with 10 g/L of the unlabeled EP-copolymer to eliminate the intermolecular interactions between Py-EP molecules. The ratio $I_E/I_M$ obtained at a low (L) concentration of the pyrene-labeled macromolecule is referred to as $(I_E/I_M)^L$. $(I_E/I_M)^L$ reflects solely intramolecular pyrene excimer formation corresponding to a low $[Py]_{loc}$. The $(I_E/I_M)^H$ and $(I_E/I_M)^L$ ratios were determined as a function of temperature and they are shown in FIGS. 1c and d, respectively. Equation 1 was used to calculate $f_{inter}$ from the $(I_E/I_M)^H$ and $(I_E/I_M)^L$ ratios. The molar fractions $f_{inter}$ of pyrene labels forming excimer intermolecularly for the Py-EP(SM) sample are shown in FIG. 2.

$$f_{inter} = \frac{(I_E/I_M)_H - (I_E/I_M)_L}{(I_E/I_M)_H} \tag{1}$$

A set of $I_E$, $I_M$, $I_E/I_M$, and $f_{inter}$ values for Py-EP(SM) are provided in Table 1.

TABLE 1

$I_E$, $I_M$, $I_E/I_M$, and $f_{inter}$ for Py-EP(SM) in toluene.

| Temp (°C.) | $(I_E)^H$ | $(I_M)^H$ | $(I_M/I_E)^H$ | $(I_E)^L$ | $(I_M)^L$ | $(I_M/I_E)^L$ | $f_{inter}$ |
|---|---|---|---|---|---|---|---|
| −30 | 1272947 | 2350992 | 1.85 | 1298397 | 524773 | 0.40 | 0.78 |
| −25 | 1378869 | 2180805 | 1.58 | 1121567 | 529523 | 0.47 | 0.70 |
| −20 | 1285102 | 2343356 | 1.82 | 1007415 | 546022 | 0.54 | 0.70 |
| −15 | 1323819 | 2308648 | 1.74 | 911821 | 540941 | 0.59 | 0.66 |
| −10 | 1397849 | 2245052 | 1.61 | 734283 | 542840 | 0.74 | 0.54 |
| −5 | 1460675 | 2158252 | 1.48 | 677983 | 523242 | 0.77 | 0.48 |
| 0 | 1611012 | 2022191 | 1.26 | 598534 | 508558 | 0.85 | 0.32 |
| 5 | 1540897 | 2029830 | 1.32 | 548738 | 508984 | 0.93 | 0.30 |
| 10 | 1534655 | 2030398 | 1.32 | 505831 | 504619 | 1.00 | 0.25 |
| 15 | 1381815 | 1959741 | 1.42 | 488696 | 525855 | 1.08 | 0.24 |
| 20 | 1310812 | 2035570 | 1.55 | 459045 | 521528 | 1.14 | 0.27 |
| 25 | 1336024 | 2086905 | 1.56 | 524854 | 584298 | 1.11 | 0.29 |

To demonstrate the importance of ($f_{inter}$), amorphous polyethylene-propylene copolymer was analyzed using the above-described method. Table 2 below shows an exemplary relationship between ($f_{inter}$) and gelation.

TABLE 2

$f_{inter}$ Impact on Gelation

| Polymer | Polymer |
|---|---|
| ƒ(inter) of polymer | 0.31 |
| Temperature | −30° C. |
| Lubricant oil containing the polymer @ ~1.0 wt % | |
| Gelation test | pass |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method for identifying a viscosity index improver suitable for use in a lubricant composition, the method comprising:
   (a) providing a first solution comprising a candidate polymer that is labeled by a fluorescent dye,
   (b) providing a second solution comprising the labeled candidate polymer, wherein the concentration of the labelled polymer in the second solution is lower than the concentration of the labelled polymer in the first solution, (c) measuring fluorescence intensities of excimers ($I_E$) and fluorescence intensities of monomers ($I_M$) of the first and second solutions at a predetermined temperature, (d) determining a level of intermolecular interaction of the candidate polymer based on a formula set forth as:

$$f_{inter}=[(I_E/I_M)^H-(I_E/I_M)^L]/(I_E/I_M)^H,$$

in which $f_{inter}$ is the fraction of intermolecular interaction relative to the total molecular interaction which includes intermolecular and intra molecular interactions, $(I_E/I_M)^H$ represents the fluorescence intensity ratio of excimer to monomer of the first solution, and $(I_E/I_M)^L$ represents the fluorescence intensity ratio of excimer to monomer of the second solution; and (e) selecting the candidate polymer as a viscosity index improver for use in a lubricant composition, if the $f_{inter}$ value of the candidate polymer is lower than 0.8.

2. The method of claim 1, wherein the candidate polymer is identified as a viscosity index improver suitable for use in a lubricant composition if it has a $f_{inter}$ value lower than 0.7.

3. The method of claim 2, wherein the candidate polymer is identified as a viscosity index improver if it has a $f_{inter}$ value lower than 0.5.

4. The method of claim 1, wherein the concentration of the labelled polymer in the first solution is at least 1 g/L and the concentration of the labelled polymer in the second solution is up to 1 g/L.

5. The method of claim 1, wherein the second solution further comprises an unlabeled polymer at a concentration of at least 1 g/L.

6. The method of claim 5, wherein the unlabeled polymer is the same as the labeled polymer.

7. The method of claim 5, wherein the unlabeled polymer is different from the labeled polymer.

8. The method of claim 1, wherein the labelled polymer contains 10-1,000 µmol of the fluorescent dye per gram of the polymer.

9. The method of claim 8, wherein the first solution contains 10 to 500 µmol of the fluorescent dye per gram of the polymer.

10. The method of claim 8, wherein the second solution contains 10 to 500 µmol of the fluorescent dye per gram of the labelled polymer.

11. The method of claim 1, wherein the fluorescent dye is pyrene.

12. The method of claim 1, wherein $I_M$ and $I_E$ are measured by a spectrofluorometer.

13. The method of claim 1, wherein the predetermined temperature ranges from about −30° C. to about 25° C.

14. A method for identifying a viscosity index improver suitable for use in a lubricant composition, the method comprising:

(a) providing a first solution comprising a candidate polymer that is labeled by a fluorescent dye, (b) providing a second solution comprising the labelled polymer and an unlabeled polymer, wherein the concentration of the labelled polymer in the second solution is lower than or the same as the concentration of the labelled polymer in the first solution and the concentration of the labelled polymer in the second solution is lower than or the same as the concentration of the unlabeled polymer in the second solution, (c) measuring fluorescence intensities of excimers ($I_E$) and fluorescence intensities of monomers ($I_M$) of the first and second solutions at a predetermined temperature, (d) determining a level of intermolecular interaction of the candidate polymer based on the formula set forth as:

$$f_{inter}=[(I_E/I_M)^H-(I_E/I_M)^L]/(I_E/I_M)^H,$$

in which $f_{inter}$ is the fraction of intermolecular interaction relative to the total molecular interaction which includes intermolecular and intra molecular interactions, $(I_E/I_M)^H$ represents the fluorescence intensity ratio of excimer to monomer of the first solution, and $(I_E/I_M)^L$ represents the fluorescence intensity ratio of excimer to monomer of the second solution; and (e) selecting the candidate polymer as a viscosity index improver for use in a lubricant composition, if the $f_{inter}$ value of the candidate polymer is lower than 0.8.

15. The method of claim 14, wherein the concentration of the labelled polymer in the first solution is 10 mg/L-10 g/L, the concentration of the labelled polymer in the second solution is 1 mg/L-1 g/L, and the concentration of the unlabeled polymer in the second solution is 2-100 times that of the labelled polymer in the second solution.

16. The method of claim 14, the concentration of the unlabeled polymer in the second solution is ten times that of the labelled polymer in the second solution.

* * * * *

UNITED STATES PATENT AND TRADEMARK OFFICE
CERTIFICATE OF CORRECTION

PATENT NO. : 9,354,180 B2
APPLICATION NO. : 14/854357
DATED : May 31, 2016
INVENTOR(S) : Sheng Jiang et al.

Page 1 of 1

It is certified that error appears in the above-identified patent and that said Letters Patent is hereby corrected as shown below:

Title page, Item (57) should read:

(57)               ABSTRACT

The present invention relates to methods for determining the level of intermolecular interaction of a polymer based on the fraction of intermolecular interaction ($f_{inter}$) relative to the total molecular interaction, which includes both inter- molecular and intramolecular interactions. Further provided herein is a method of identifying a suitable viscosity index improver based on the value of $f_{inter}$. The identified suitable viscosity index improver can be used in a lubricating oil composition for, *e.g.*, a power transmission system.

Signed and Sealed this
Second Day of August, 2016

Michelle K. Lee
*Director of the United States Patent and Trademark Office*